(12) United States Patent
Diep et al.

(10) Patent No.: US 7,736,337 B2
(45) Date of Patent: Jun. 15, 2010

(54) SEALING CATHETER HUB ATTACHMENT

(75) Inventors: Nhut M Diep, Hartford, CT (US); David J Goral, Brookfield, CT (US); Alan D King, Burlington, CT (US); Thomas T Koehler, Simsbury, CT (US)

(73) Assignee: Smiths Medical, ASD, Inc., Rockland, MA (US)

( * ) Notice: Subject to any disclaimer, the term of this patent is extended or adjusted under 35 U.S.C. 154(b) by 1025 days.

(21) Appl. No.: 11/276,155

(22) Filed: Feb. 16, 2006

(65) Prior Publication Data
US 2007/0191775 A1 Aug. 16, 2007

(51) Int. Cl.
*A61M 5/00* (2006.01)
(52) U.S. Cl. .................................. 604/164.01
(58) Field of Classification Search ............ 604/164.01, 604/164.07, 158, 167.01
See application file for complete search history.

(56) References Cited

U.S. PATENT DOCUMENTS

| 4,747,831 | A | | 5/1988 | Kulli |
| 4,762,516 | A | | 8/1988 | Luther et al. |
| 4,791,937 | A | * | 12/1988 | Wang .......................... 600/565 |
| 4,832,696 | A | | 5/1989 | Luther et al. |
| 4,950,252 | A | | 8/1990 | Luther et al. |
| 4,952,207 | A | | 8/1990 | Lemieux |
| 4,978,344 | A | | 12/1990 | Dombrowski et al. |
| 5,000,740 | A | | 3/1991 | Ducharme et al. |
| 5,085,645 | A | * | 2/1992 | Purdy et al. ............ 604/167.03 |
| 5,092,845 | A | | 3/1992 | Chang |
| 5,215,528 | A | | 6/1993 | Purdy et al. |
| 5,234,410 | A | * | 8/1993 | Graham et al. ......... 604/167.01 |
| 5,322,517 | A | | 6/1994 | Sircom et al. |
| 5,328,482 | A | | 7/1994 | Sircom et al. |
| 5,330,435 | A | * | 7/1994 | Vaillancourt ........... 604/167.01 |
| 5,407,431 | A | | 4/1995 | Botich et al. |
| 5,458,640 | A | | 10/1995 | Gerrone |
| 5,558,651 | A | | 9/1996 | Crawford et al. |
| 5,810,785 | A | | 9/1998 | Bogert et al. |
| 5,817,058 | A | * | 10/1998 | Shaw .......................... 604/110 |
| 5,846,227 | A | | 12/1998 | Osterlind |
| 5,911,710 | A | | 6/1999 | Barry et al. |
| 6,595,954 | B1 | * | 7/2003 | Luther et al. ................. 604/110 |
| 6,652,486 | B2 | | 11/2003 | Bialecki et al. |
| 2004/0204691 | A1 | | 10/2004 | Yashiro et al. |
| 2004/0225260 | A1 | | 11/2004 | Villa et al. |
| 2005/0090779 | A1 | | 4/2005 | Osypka |

FOREIGN PATENT DOCUMENTS

| EP | 0352928 A1 | | 1/1990 |
| EP | 451040 A1 | * | 10/1991 |
| EP | 0875262 A2 | | 4/1998 |
| EP | 1466644 A2 | | 10/2004 |
| EP | 1634615 A1 | | 3/2006 |
| FR | 2475903 | | 8/1981 |
| GB | 2067075 | | 7/1981 |
| JP | 1995024071 | | 1/1995 |

* cited by examiner

OTHER PUBLICATIONS

International Search Report and Written Opinion for PCT/US2007/062191 (10 pages).

*Primary Examiner*—Nicholas D Lucchesi
*Assistant Examiner*—Aarti B Berdichevsky
(74) *Attorney, Agent, or Firm*—Wood, Herron & Evans, LLP

(57) ABSTRACT

A generally rigid molded plastic catheter hub attachment (16, 52, 74) includes one or more co-molded elastomeric gaskets (22, 58).

22 Claims, 2 Drawing Sheets

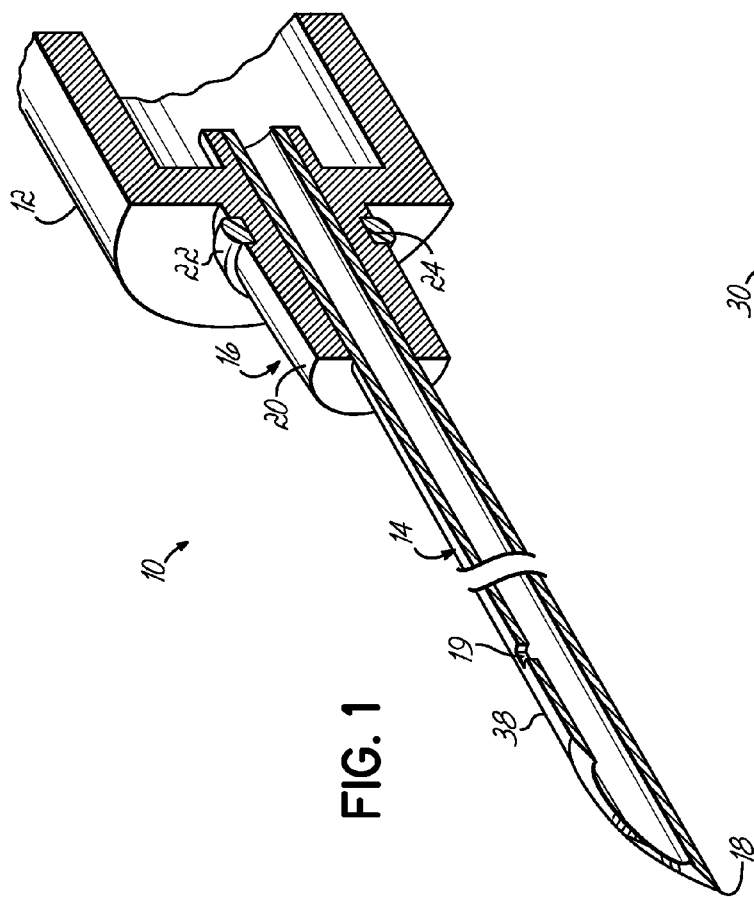
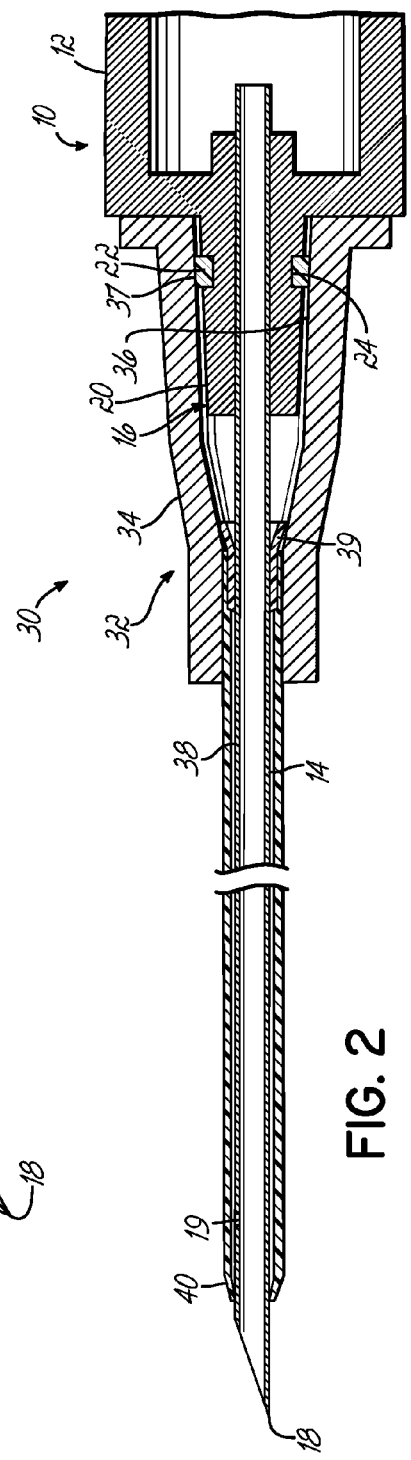
FIG. 1
FIG. 2

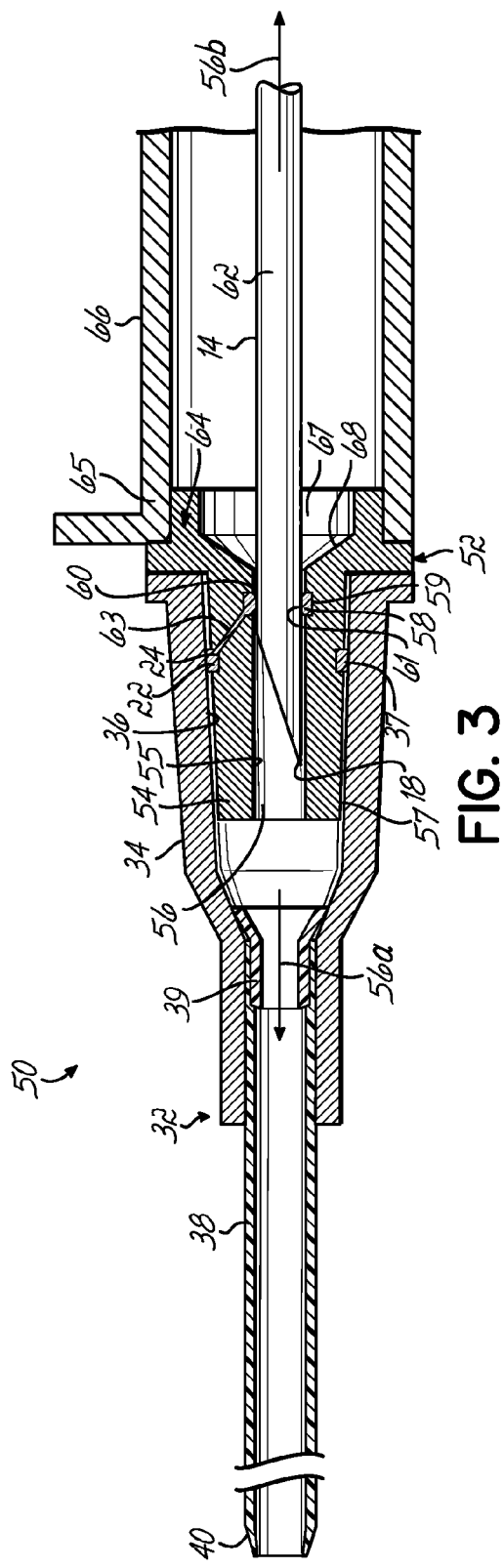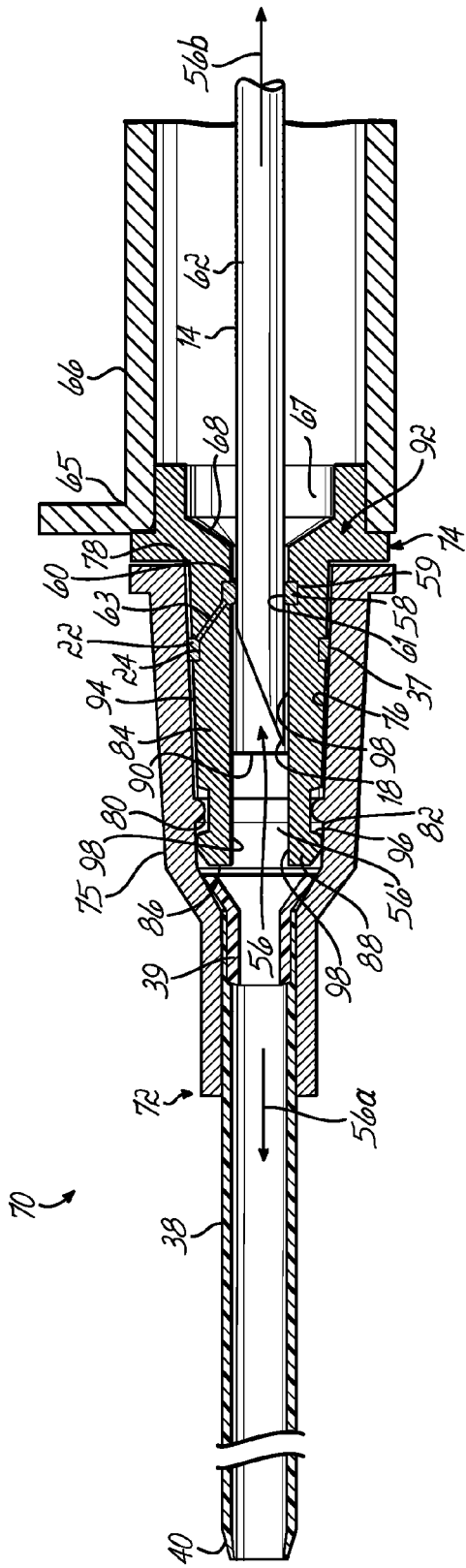

SEALING CATHETER HUB ATTACHMENT

FIELD OF THE INVENTION

The present invention relates to devices which couple to catheter hubs, and more particularly, to a catheter hub attachment of a catheter insertion device.

DESCRIPTION OF PRIOR ART

Over-the-needle catheters are well known in the art. In such devices, a cannula needle projects through a catheter tube with its sharp tip projecting out of the end of the tube. The sharp tip of the needle is used to pierce the skin and the blood vessel so as to carry the end of the catheter tube into the vessel. Once in place, the needle is withdrawn, leaving the catheter in place for administration or withdrawal of fluids, such as by connection with the female luer taper of the now-exposed catheter hub.

The needle is typically supported by a hub or other housing which has a catheter hub attachment for removably attaching the housing to the catheter hub. The catheter hub attachment may be in the form of a rigid, tapered nose, such as a male slip luer, the exterior wall of which is adapted to frictionally engage against a generally, rigid inner female luer taper of the catheter hub. In some devices, in order to protect against needle sticks after withdrawal of the needle from the catheter, the needle might be slidably movable through the catheter hub attachment so that the needle may be withdrawn into a needle guard or a housing containing needle gripping and/or shielding structure. In the latter type of devices, the catheter hub attachment may still be defined by a rigid nose, but with an internal passageway for the needle to slidingly pass through. Alternatively or additionally, the catheter hub attachment nose may include a pair of flexing arms adapted to resiliently engage the inner wall of the catheter hub with the passageway also extending through the space between the arms for the needle to slide therethrough.

One problem with the prior catheter hub attachments, however, is that they might allow for blood leakage during or after insertion of the catheter into the patient. For example, the rigid nose exterior wall portion is generally continuous in circumferential extent and sized to interfit with the inner wall of the catheter hub so as to create an annular plastic-to-plastic seal in accordance with luer standards. However, the seal is not always reliable. Moreover, the hold between the catheter hub and the attachment nose is based on friction, and so in those cases where the nose and catheter hub need to be rotated relative to one another, as sometimes arises in order to properly thread the catheter into the blood vessel, the seal may be overcome. Consequently, with rigid nose catheter hub attachments, blood might migrate between the inner wall of the catheter hub and the exterior wall of the nose, thus creating a risk of blood leakage.

Where the nose includes the pair of arms, a proximal portion of the attachment may still define a generally rigid circumferentially continuous exterior surface for interfitting with the catheter hub inner wall for purposes of creating the seal. But that seal may also not be adequate.

Additionally, where the catheter hub attachment is designed to allow the needle to slidingly pass therethrough, blood might backflow between the needle and the passageway. Efforts to reduce such leakage have involved relatively complex seals, such as blown-in extruded gaskets or formed-in-place UV curable and breakable seals such as shown in U.S. Pat. Nos. 5,810,785 and 5,092,845, respectively. While the foregoing are believed to create a more reliable seal between the needle and catheter hub attachment, they are not without their drawbacks.

SUMMARY OF THE INVENTION

The present invention provides an improved seal for a catheter hub attachment of a needle catheter insertion device. To that end, and in accordance with the principles of the present invention, a co-molded elastomeric gasket is integrally formed into the catheter hub attachment either at the exterior wall which is to fit within the inner wall of the catheter hub and/or in the passageway through which the needle is to slide. The elastomeric gasket material may be medical grade silicone. The elastomeric and integral nature of the co-molded gasket(s) results in a seal that is reliable, yet also is less likely to fail during relative rotation of the catheter hub attachment and the catheter hub. Moreover, co-molding the elastomeric gasket material into the otherwise generally rigid plastic of the catheter hub attachment presents many advantages over previous efforts to provide seals for catheter hub attachments.

By way of example, and not limitation, the co-molded elastomeric gasket in the passage is believed to provide a more reliable and tolerant seal than the prior blown-in place or formed-in place seals. The co-molded elastomeric gasket (s) also provide advantages in manufacture and cost over separately provided gaskets, such as O-rings or the like, while providing O-ring like seal advantages. Further, the gasket(s) can be formed to the catheter hub attachment with conventional co-molding techniques, thus eliminating the need for multiple, separate manufacturing steps or machines. Moreover, where both the gasket at the exterior wall and the gasket in the passageway are to be included, they may both be formed at the same time.

In addition to the foregoing, where the catheter hub attachment includes a pair of arms, the co-molded elastomeric gasket(s) do not interfere with the operation of the arms in serving to hold the catheter hub attachment to the catheter hub in a manner that allows for easy removal of the catheter hub attachment from the catheter hub after the insertion needle has been withdrawn. Similarly, the arms help improve the hold of the catheter hub attachment to the catheter hub thereby helping maintain the seal.

By virtue of the foregoing, there is thus provided an improved seal for a catheter hub attachment of a needle catheter insertion device. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

FIG. 1 is a perspective, cross-section view of a needle with a catheter hub attachment nose having a co-molded elastomeric gasket in the exterior wall of the nose in accordance with the principles of the present invention;

FIG. 2 is a cross-section view of the needle of FIG. 1 with a catheter assembly to define a catheter insertion device;

FIG. 3 is a partial, cross-section view of a catheter insertion device with a rigid nose catheter hub attachment and a slidable needle and having co-molded elastomeric gaskets in accordance with the principles of the present invention; and FIG. 4 is a partial, cross-section view of a catheter insertion device with a split arm catheter hub attachment and a slidable needle and having co-molded elastomeric gaskets in accordance with the principles of the present invention.

DETAILED DESCRIPTION OF THE DRAWINGS

With reference to FIG. 1, there is shown a needle device 10 having a needle housing 12, such as a flash chamber or the like, and a catheter insertion needle 14 rigidly affixed thereto so as to extend from the nose 16 of housing 12 to a sharp tip end 18. Needle 14 may optionally have a vent 19 formed proximal of tip end 18. Nose 16, alone or in conjunction with the rest of needle housing 12, defines a catheter hub attachment. Nose 16 advantageously has a tapered, circumferentially continuous exterior wall 20 such as defined by a male luer taper. Needle housing 12 is typically made by molding plastic, such as polycarbonate thermoplastic, to define a generally rigid plastic member. In accordance with the principles of the present invention, needle housing 12 may be molded and an annular elastomeric gasket 22, which may advantageously be comprised of medical grade silicone, may be co-molded with exterior wall portion 20, such as in annular recess 24 thereof, using conventional co-molding techniques. However, due to the co-molding, gasket 22 becomes an integral part of needle housing 12, and especially nose 16 thereof.

Due to the elastomeric nature of co-molded gasket 22, gasket 22 will have more resiliency than the rest of nose 16 and so may be used to define, or add to, a seal. To that end, and with reference to FIG. 2, a catheter insertion device 30 includes needle device 10 mounted to a catheter assembly 32 having a catheter hub 34 with an inner wall 36 defining a female luer taper into which male luer taper nose 16 fits and to which gasket 22 sealingly engages as at 37. To that end, gasket 22 is co-molded to have a slightly larger outer diameter than the inner diameter of catheter hub inner wall 36 at the area of seal 37. Catheter assembly 32 also includes a catheter tube 38 held to catheter hub 34 with an eyelet 39 so as to extend from catheter hub 34, with needle 14 extending through catheter tube 38 so that the sharp tip end 18 of needle 14 extends out from the beveled, distal tip end 40 of catheter tube 38. Needle 14 and tube 38 may allow blood to pass therebetween from vent 19. Catheter insertion device 30 may be used to install catheter tube 38 into a patient's blood vessel (not shown) in conventional manner, and needle housing 12 and catheter hub 34 may be relatively rotated as needed. Any blood (not shown) that might attempt to pass between needle 14 and catheter tube 38 will encounter the seal 37 at gasket 22 by which to forestall migration of the blood (not shown) between exterior wall 20 of catheter hub attachment nose 16 and inner wall 36 of catheter hub 34. Gasket 22 provides an improved and more reliable seal than would have otherwise been provided by the rigid plastic-to-plastic interfitting of nose exterior wall 20 and catheter hub inner wall 36 alone. Although not shown for sake of clarity, the latter may still be provided in addition to the seal provided by gasket 22 interacting with catheter hub inner wall 36, if desired.

With reference to FIG. 3, a catheter insertion device 50 includes a catheter assembly 32 like that shown in FIG. 2 (and having like-numbered parts) and a catheter hub attachment 52. Catheter hub attachment 52 has a distal nose 54 (similar to nose 16 shown in FIGS. 1 and 2) with an inner wall 55 defining a passageway 56 sized to slidably receive needle 14 therethrough as indicated by arrows 56a and 56b, and an exterior, male luer slip taper wall 57 to fit within catheter hub 34. Distal nose 54 has co-molded elastomeric gasket 22 integrally associated with exterior wall 57 (such as in recess 24) to form the seal 37 with inner wall 36 of catheter hub 34 as described in connection with nose 16 above. But, catheter hub attachment 52 may also, alternatively or additionally, include another co-molded elastomeric gasket 58 integrally associated with the inner wall 55 of catheter hub attachment 52 (such as in annular recess 59 of wall 55). Gasket 58 has an entry aperture 60 to also define a seal, as at 61, against shaft surface 62 of needle 14 (which, in this embodiment need not include the vent 19) as it slides through (into or out of) passageway 56 of catheter hub attachment 52. To that end, gasket 58 is formed to have an inner diameter of aperture 60 slightly smaller than the nominal outer diameter of needle shaft 62. Gaskets 22 and 58 may be co-molded at the same time, such as by first moulding catheter hub attachment 52 of rigid plastic with one or more ports 63 (only one shown) communicating between recesses 24 and 59, followed by co-molding the elastomeric material into recess 24 and, via port(s) 63, into recess 59.

The proximal end 64 of catheter hub attachment 52 may form, or be attached to, the distal side 65 of a needle guard or needle shield housing 66. Housing 66 may take on numerous forms and possibly include a wide variety of needle tipping and/or needle tip shield structures (not shown). By way of example, such housings can include the needle guard housing of the PROTECTIV Safety I.V. Catheter being marketed by Medex, Inc., the assignee hereof, a version thereof with fluid path access as shown and described in the commonly assigned and concurrently filed U.S. patent application entitled "Enclosed Needle Device With Fluid Path Access", or housing structure to grip and/or block the needle as shown in U.S. Pat. Nos. 4,762,516; 4,747,831; 4,978,244; 5,215,528; 5,322,517; 5,328,482; and 5,558,651; European Patent No. 0,352,928 B2; and/or U.S. patent application Ser. Nos. 10/905,047 and 10/906,171.

In the catheter hub attachment 52 shown in FIG. 3, gasket 58 is formed in passageway 56 distal of the proximal end 64, although it will be appreciated that an elastomeric gasket could additionally or alternatively be within the proximal end 64 such as by being co-molded as a larger gasket in extension 67 of passageway 56 such as in the mouth 68 of proximal end 64. Gasket 58 provides an easily manufactured, reliable and tolerant seal 61 to needle 14 to thereby reduce or eliminate backflow of blood (not shown) over needle shaft 62 through passageway 56.

With reference to FIG. 4, there is shown an alternate catheter insertion device 70 having catheter assembly 72 and catheter hub attachment 74. Catheter assembly 72 has a catheter hub 75 within inner wall 76 which may advantageously define a female luer taper slip extending from hub opening 78, and an annular rib 80 distally of proximal opening 78 thereof to define an annular space 82 distal of rib 80 for purposes to be explained hereafter. Catheter hub attachment 74 has a distal nose 84 which includes a pair of arms 86, 88 extending from a tapered, tubular nose segment 90 coupled to proximal end 92 (the latter being akin to proximal end 62 of FIG. 3). The outer aspects of arms 86, 88 and/or nose segment 90 define exterior walls 94 designed to fit within catheter hub 75, with arms 86, 88 adapted to flex. In particular, one or both of arms 86, 88 may include a detent 96 which normally extends to an outer diametrical distance larger than the inner diameter defined at rib 80. As catheter hub attachment 74 is inserted into catheter hub 75, arm 86 and/or arm 88 flexes inwardly to ride over rib 80, and then flex back out to provide a weak hold of catheter hub attachment 74 against catheter hub inner wall 76.

Advantageously, the inner surfaces 98 of arms 86, 88 are normally spaced apart a distance that is only slightly larger than the outer diameter of needle shaft 62. Needle passageway 56 extends between inner surfaces 98 of arms 86, 88 as at passageway portion 56'. With needle 14 pushed distally (in the direction of arrow 56a) so that it passes through passageway portion 56' to extend fully between arms 86, 88 (and advantageously to extend sharp tip end 18 out of catheter tube 38), the close fit between needle shaft 62 and arms 86, 88 limits the ability of arms 86, 88 to flex inwardly. As a consequence, the force required to pull catheter hub attachment 74 away from catheter hub 75 is increased while needle shaft 62 is between arms 86, 88, but much weaker when shaft 62 is not present therebetween (such as by moving needle 14 in the diameter of arrow 56b to the position shown, for example, in FIG. 4). Also, even with the weak forces involved with needle 14 in the position shown in FIG. 4, catheter hub attachment 74 is held to catheter hub 75 to help improve the sealing feature of gasket 22 until catheter hub attachment 74 is removed from catheter hub 75. Where housing 66 is like the needle guard housing of the PROTECTIV Safety I.V. Catheter mentioned earlier, a cooperating locking mechanism may be employed as shown and described in the commonly assigned and concurrently filed U.S. patent application entitled "Enclosed Needle Device with Duckbill Release Mechanism".

Distal nose 84 includes integral, co-molded elastomeric gasket 22 with exterior wall 94 such as in recess 24 of tubular nose segment 90, and passageway 56 includes co-molded elastomeric gasket 58, both of which may be formed, and which operate, as described in connection with FIG. 3. However, some prior seals, such as a formed-in-place UV curable gasket, could interfere with the functioning of arms 86, 88; co-molded gasket 58 will not likely do so.

In use, needle 14 is placed (in the direction of arrow 56a, for example) so that tip 18 extends out from catheter tube 38. The exposed sharp tip 18 of needle 14 is used to pierce the skin and blood vessel of a patient (not shown) to place catheter tube 38 therein. Gasket 22 provides a seal against blood (not shown) attempting to migrate out of the catheter hub 34 or 75. Needle 14 is then withdrawn, either by pulling it out with housing 12 and catheter hub attachment 16 if needle 14 is affixed thereto (FIG. 2), or by pulling needle 14 through passageway 56 and thereafter pulling catheter hub attachment 52 or 74 away from catheter hub 34 or 75 (FIGS. 3 and 4). Where passageway 56 is provided, gasket 58 reduces the risk of blood (not shown) migrating through catheter hub attachment 52 or 74. With catheter hub attachment 16, 52 or 74 removed, catheter hub 34 will be exposed for use by the medical practitioner (not shown). The needle 14 and related components may then be discarded.

By virtue of the foregoing, there is thus provided an improved seal for a catheter hub attachment of a needle catheter insertion device.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, detent(s) 96 of arms 86, 88 are shown as holding behind rib 80 in space 82. Alternatively or additionally, inner wall 76 of catheter hub 75 could have an annular recess (not shown) at space 82 into which the detent 96 snaps when arms 86, 88 flex to the normal state. Further, a metal needle shield clip (not shown) could be provided over needle shaft 62 and sized to fit within catheter hub 34 or 75 (the latter may require size changes to one or more of the plastic components, however) such as shown in U.S. Pat. No. 6,652,486 B2. Additionally, although only one of gasket 22 or gasket 58 may be provided, multiple such gaskets may be defined during the co-molding process if desired. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A catheter hub attachment of a catheter insertion device comprising:
   a generally rigid molded plastic nose having an internal passageway therethrough and through which a catheter insertion needle can slidingly pass and having an exterior wall sized to fit within a catheter hub;
   an elastomeric first gasket integrally associated with the internal passageway whereby to create a seal around a catheter insertion needle passing through the internal passageway; and
   an elastomeric second gasket integrally associated with the exterior wall whereby to create a seal with a portion of an internal wall of a catheter hub into which the nose is fitted.

2. The catheter hub attachment of claim 1, the nose having a proximal portion adapted to be coupled to a needle guard housing.

3. The catheter hub attachment of claim 2, the first gasket being spaced distally from the proximal portion.

4. The catheter hub attachment of claim 1, the first gasket extending from a recess confronting the passageway.

5. The catheter hub attachment of claim 1, the second gasket extending from a recess in the exterior wall.

6. The catheter hub attachment of claim 1, the nose including a generally continuous tubular taper.

7. The catheter hub attachment of claim 6, the exterior wall defining at least a portion of the tubular taper.

8. The catheter hub attachment of claim 1, the nose including a pair of arms, the arms defining a portion of the passageway therebetween.

9. The catheter hub attachment of claim 1 further comprising a port communicating between the first and second gaskets.

10. The catheter hub attachment of claim 1 in combination with a catheter insertion needle received in the passageway.

11. The catheter hub attachment of claim 1, the nose having a proximal end and a distal end opening, with the internal passageway communicating between the proximal end and the distal end opening such that the catheter insertion needle can slidingly pass into and out of the opening, the first gasket being completely proximal of the distal end opening.

12. A catheter hub attachment of a catheter insertion device comprising:
   a generally rigid molded plastic nose having a proximal end and a distal end opening, the nose having an internal passageway therethrough communicating between the proximal end and the distal end opening and through which a catheter insertion needle can slidingly pass into and out of the opening, the nose further having an exterior wall sized to fit within a catheter hub; and
   an elastomeric first gasket being completely proximal of the distal end opening and integrally associated with the internal passageway whereby to create a seal around a catheter insertion needle passing through the internal passageway.

13. The catheter hub attachment of claim 12, the nose having a proximal portion adapted to be coupled to a needle guard housing.

14. The catheter hub attachment of claim 13, the gasket being spaced distally from the proximal portion.

15. The catheter hub attachment of claim 12, the gasket extending from a recess confronting the passageway.

16. The catheter hub attachment of claim 12 in combination with a catheter insertion needle received in the passageway.

17. A catheter hub attachment of a catheter insertion device comprising:

a generally rigid molded plastic nose having an exterior wall sized to fit within a catheter hub;

a needle extending from the nose; and an elastomeric gasket integrally associated with the exterior wall whereby to create a seal with a portion of an internal wall of a catheter hub into which the nose is fitted.

18. The catheter hub attachment of claim 17, the gasket extending from a recess in the external wall.

19. The catheter hub attachment of claim 17, the nose including a generally continuous tubular taper.

20. The catheter hub attachment of claim 19, the exterior wall defining at least a portion of the tubular taper.

21. The catheter hub attachment of claim 17, the nose including a pair of arms, the arms defining a portion of the passageway therebetween.

22. The catheter hub attachment of claim 17, the nose including an internal passageway, the needle slidingly passing through the nose internal passageway.

* * * * *